(12) United States Patent
Agreli et al.

(10) Patent No.: US 12,376,960 B2
(45) Date of Patent: Aug. 5, 2025

(54) MITRAL STENT

(71) Applicant: P+F Products + Features GmbH, Vienna (AT)

(72) Inventors: Guilherme Agreli, Sao Jose de Rio Preto (BR); Katharina Kiss, Vienna (AT); Siegfried Einhellig, Vienna (AT)

(73) Assignee: P+F PRODUCTS + FEATURES GMBH, Vienna (AT)

( * ) Notice: Subject to any disclaimer, the term of this patent is extended or adjusted under 35 U.S.C. 154(b) by 179 days.

(21) Appl. No.: 17/666,926

(22) Filed: Feb. 8, 2022

(65) Prior Publication Data

US 2022/0257374 A1 Aug. 18, 2022

(30) Foreign Application Priority Data

Feb. 18, 2021 (EP) .................................... 21157887

(51) Int. Cl.
*A61F 2/24* (2006.01)
*A61F 2/90* (2013.01)

(52) U.S. Cl.
CPC .............. *A61F 2/2418* (2013.01); *A61F 2/90* (2013.01); *A61F 2210/0014* (2013.01); *A61F 2230/0017* (2013.01)

(58) Field of Classification Search
CPC .......... A61F 2/2418; A61F 2/246; A61F 2/90
See application file for complete search history.

(56) References Cited

U.S. PATENT DOCUMENTS

| | | | |
|---|---|---|---|
| 2003/0014105 A1* | 1/2003 | Cao ........................ | A61F 2/2409 623/2.15 |
| 2011/0301700 A1* | 12/2011 | Fish ...................... | A61F 2/0095 156/60 |
| 2012/0101572 A1* | 4/2012 | Kovalsky .............. | A61F 2/2418 623/2.19 |
| 2015/0257881 A1 | 9/2015 | Börtlein et al. | |
| 2016/0000559 A1* | 1/2016 | Chen ..................... | A61F 2/2412 623/2.15 |
| 2016/0310268 A1* | 10/2016 | Oba ....................... | A61F 2/2433 |

(Continued)

FOREIGN PATENT DOCUMENTS

CN 105726167 A * 7/2016

*Primary Examiner* — Brian A Dukert
(74) *Attorney, Agent, or Firm* — Vivacqua Crane, PLLC

(57) ABSTRACT

The invention relates to a self-expendable stent for placement at a mitral annulus that is self-expandable from an undeployed state to a deployed state comprising a stent frame having at least a first section and a second section arranged at a longitudinal axis of the stent, wherein the stent frame is formed by a plurality of endless arms, the arms being connected to one another at connection points forming a web-like structure with diamond-shaped cells; a dry valve made out of bovine pericardium arranged at least at the second section of the stent with the dry bovine pericardium being configured to be rehydrated with a solution, a skirt surrounding the dry valve and comprising at least one of bovine pericardium and polyester, and wherein, in the expanded state, a maximum outer diameter of the first section is larger than a maximum outer diameter of the second section, and wherein at least at a transition between the first section and the second section some of the endless arms extend outwardly beyond the web-like structure to form a hook, which faces the first section.

22 Claims, 4 Drawing Sheets

(56) References Cited

U.S. PATENT DOCUMENTS

| | | | |
|---|---|---|---|
| 2017/0156859 A1* | 6/2017 | Chang | A61F 2/2439 |
| 2018/0110617 A1* | 4/2018 | Howard | A61F 2/2412 |
| 2018/0250130 A1* | 9/2018 | Hariton | A61F 2/2436 |
| 2022/0061986 A1* | 3/2022 | Humair | A61F 2/2427 |

\* cited by examiner

MITRAL STENT

CROSS REFERENCE TO RELATED APPLICATIONS

This application claims the benefit of foreign priority under 35 U.S.C. § 119 of European patent application number 21157887.7, filed Feb. 18, 2021. The contents of this application are incorporated herein by reference in their entirety.

INTRODUCTION

The invention relates to a self-expendable stent for placement at a mitral annulus that is self-expandable from an undeployed state to a deployed state.

A healthy heart facilitates oxygenated blood flow to the extremities. The heart is comprised of two chambers: the right chamber and the left chamber, which manage deoxygenated and oxygenated blood respectively. Deoxygenated blood from the upper and the lower extremities, travels through both caval veins, i. e. the vena cava superior and the vena cava inferior, into the right atrium. It is pumped through the tricuspid valve and into the right ventricle. During systole, when the ventricle is full, the tricuspid valve shuts and blood is pumped from the right ventricle through the pulmonary valve into the pulmonary artery and to the lungs where it is oxygenated. Following said oxygenation, blood is pumped back to the left side of the heart, i. e. the left atrium, through the pulmonary vein. As the atrium contracts, oxygenated blood flows from the left atrium through the mitral valve into the left ventricle. During systole, when the left ventricle is full, the left ventricle ejects the blood through the aortic valve into the aorta and to the rest of the body as well as to the coronary arteries which supply the heart muscle itself.

Proper opening and closing of the atrioventricular valves is dependent on the function of all of the structures involved with leaflet function, specifically the annulus, the leaflets, the chordae tendinae, the papillary muscles and a healthy myocardial wall. During ventricular filling (diastole), the atrioventricular valves remain open and during ventricular contraction (systole), the valves close as a consequence of complete leaflet apposition. In instances where complete apposition of the leaflets is not achieved, leakage or regurgitation across the valve affects cardiac performance and health. Severe regurgitation or leakage can lead to hemodynamic deterioration and/or heart failure.

Moderate or higher tricuspid valve regurgitation affects cardiac functional performance, and is typically indicative of a broader primary disease such as left heart dysfunction. Primary dysfunction can include pulmonary hypertension, right ventricular volume overload and right ventricular disease. Similarly, mitral regurgitation or leakage is primarily due to degenerative valve disease. The presence of dysfunctional support structures also contributes to mitral regurgitation, specifically as a consequence of a heart attack (ischemic mitral regurgitation) or ventricular dilation (functional mitral regurgitation). Other causes of atrioventricular regurgitation include acquired conditions (i.e. endocarditis, rheumatic heart disease) and congenital anomalies.

Atrioventricular regurgitation also impact the caval veins leading to the atrium. During tricuspid regurgitation, pressure and flow changes in the right atrium causes the inferior vena cava (IVC) and the superior vena cava (SVC) to dilate. Additionally, veins feeding the IVC and the SVC are also impacted by these effects. Specifically, tricuspid regurgitation causes the azygos and the hepatic veins, which are located cranial and caudal to the right atrial opening respectively, to dilate. This leads to overall hemodynamic deterioration and liver dysfunction. Physical symptoms of tricuspid regurgitation include fatigue, loss of appetite and abdominal fullness. Similarly, mitral regurgitation impacts the pulmonary vein and can cause fluid buildup in the lungs. Chronic mitral regurgitation often leads to left ventricular remodeling or dilation of the left ventricle. Physical symptoms of mitral regurgitation include fatigue, decreased exercise tolerance, shortness of breath, and swollen feet. If left untreated, either atrioventricular severe regurgitation can lead to pulmonary hypertension, atrial fibrillation or heart failure.

On use of transcatheter valves to treat e.g. mitral diseases, these modify the anatomy of the structures surrounding the mitral valve, deforming the aortic valve or lead to an occlusion of the coronary arteries or veins. A deformation of anatomical structures can lead to a malfunction of the heart, including the aortic valve. Other complications brought about by an implantation of a replacement mitral valve is a change in the flow properties of the blood exiting the mitral valve due to the design of the replacement valve or thrombus formation in the atrial portion respectively. Moreover, if the atrioventricular valve is not placed correctly, this cannot seal the ventricles from the atria correctly such that the underlying pathology is not treated correctly, creating a paravalvular leakage.

One drawback of existing technologies is leakage around the valve, termed paravalvular leakage (PVL). PVL is usually a result of at least one of the following malpositioning of an implant, calcium interference with implant expansion, incorrect sizing of the implant and/or implant migration.

Therefore, biological tissues are widely used to make prosthetic replacements for heart valves and blood vessels as well as for transcatheter heart valves. They are connective tissues comprising collagen as the main component. Among these tissues, bovine pericardium is one of the most widely employed. Pericardial tissue is the sac surrounding the heart which provides a natural barrier to infection for the heart and prevents adhesion to the surrounding tissue. The pericardium also serves mechanical roles, for example, by preventing over dilation of the heart, maintaining the correct anatomical position of the heart, and regulating the pressure to volume ratio in the left ventricle during diastole. The structure of the tissue determines its behavior under loading in both conditions physiologic to the pericardium and as a prosthetic device.

However, biological tissues obtained from the abattoir, in particular porcine and bovine cadavers, begin to degrade immediately. Therefore, the storage of such materials has proven to be difficult. For this purpose, a biological tissue, such as e.g. bovine or porcine pericardium or a heart valve, is usually chemically treated to improve its mechanical performance and immunogenic properties, reduce thrombogenicity and degradation, preserve sterility, and prolong the allowable storage period.

Accordingly, biological tissues are known which can be used as bioprosthetic devices that can be stored dry before used for clinical applications. Additionally, special care has to be taken in connection with the preparation methods in order to avoid the formation of degenerative calcific deposits. Calcification, in particular pathologic calcification, of soft biological tissues due to deposition of calcium phosphate mineral salts in an implanted tissue is undesirable and the deposition of the calcific deposits can have severe consequences on device performance. Calcification of implants can lead to stiffening, structural instability and ultimately to device failure.

Although there are difficulties in the usage of biological tissues, their performance inside a human body has proven to be significantly better.

SUMMARY

For this reason, it is an object of the present invention to make available a stent by means of which PVL is prevented as far as possible and with which trauma during surgery can be reduced, so that the stent can also be used with elderly patients. This object is solved by the subject matter of independent claim 1.

Such a self-expandable stent for placement at a mitral annulus is self-expandable from an undeployed state to a deployed state and comprises a stent frame having at least a first section and a second section arranged at a longitudinal axis of the stent, wherein the stent frame is formed by a plurality of endless arms, the arms being connected to one another at connection points forming a web-like structure with diamond-shaped cells. The stent further comprises a dry valve made out of bovine pericardium arranged at least at the second section of the stent with the dry bovine pericardium being configured to be rehydrated with a solution, and a skirt surrounding the dry valve and comprising at least one of bovine pericardium and polyester, preferably both materials. In the expanded state, a maximum outer diameter of the first section is larger than a maximum outer diameter of the second section. Also, at least at a transition between the first section and the second section some of the endless arms extend outwardly beyond the web-like structure to form a hook, which faces the first section.

The stent for an implant or prosthesis described herein is in particular suitable for the treatment of mitral valve diseases via minimally invasive transcatheter implantation to replace a defective mitral valve.

In this connection it is noted that throughout the application text the expressions "first section" and "second section" refer to the upper section and lower section of the stent as depicted in FIG. 1, respectively. That is, the first section of the stent relates to the first part of the deployed stent in the flow direction of the blood, i. e. to the part through which the blood enters when the stent is deployed at the mitral valve of a patient. Consequently, the second section relates to the second part in the flow direction of the blood including the part through which the blood exits the stent.

The stent comprises a plurality of endless arms which build the stent frame comprising two sections, i.e. the first section and the second section. The expansion of the stent is made possible by the plurality of arms that are interconnected in such a way that following the expansion they adapt to the anatomical need of the location of the stent. In this way the design of such a stent is adapted to accommodate the anatomical needs and implantation locations. The stent furthermore exists of a self-expandable stent frame. Moreover, between 6 and 50 arms can be provided to form the stent frame.

The plurality of arms is connected to one another at connection points and form a web-like structure made out of plurality of diamond-shaped stent cells.

In this connection it should be noted that the parts of the plurality of arms forming sides of the stent cells are linear, such that the formed stent cells comprise a diamond shape.

Such shapes can be manufactured in a simple manner and provide the stent frame with an increased stability and flexibility.

Due to the increased flexibility of the stent, the implant comprising such a stent can be placed more accurately within the heart thereby improving the function of the implant due to the increased apposition to the native annular anatomy using appropriate design options. Flexibility within the stent is intended to aid implant trackability and deployability within the vasculature. In addition, the ability to steer the implant from the access site to the implant site is improved due the increased flexibility even in the undeployed state of the stent. This is necessary to reduce trauma to a patient during implantation, and to ensure accurate implant placement. The reduction of trauma to a patient also makes the surgery less critical so that this kind of implant can also be provided in patients who were previously not operable due to the too high a risk associated with the implantation of prior art designs.

Additionally, in the expanded state, a maximum outer diameter of the first section is larger than a maximum outer diameter of the second section. Such a design can further improve the function of the implant by enabling an interference fit between the stent and the mitral valve of the patient's heart.

The invention is further characterized in that at least at a transition between the first section and the second section some of the endless arms extend outwardly beyond the web-like structure to form a hook, which faces the first section. That is, some of the arms interrupt the web-like structure by extending outwardly beyond said structure of a main body of the stent frame such that the endless arms extending beyond the main body form a respective hook. Since said arms forming the hooks interrupt the web-like structure, the cell underneath said respective hook, i. e. the cells that lie radially more inside compared to the hooks, comprise a significantly bigger area than the cells forming the web-like structure. Nevertheless, said bigger cells are also interconnected with the rest of the stent frame.

A tip of said hooks faces the first section such that the hooks are aligned contrary to the flow direction of the blood inside the patient's heart. Hence, said tips face the left atrium of the patient's heart. Such hooks can act as an anchor to contribute to a better fixation of the stent at the position of the native mitral valve of a patient, in particular at the annulus of the valve.

The stent comprises a dry valve made of bovine pericardium, which upon final placement at the aortic artery can be rehydrated with a solution such as a saline solution. Hence, a pericardium as an animal biological tissue material is used, in particular obtained from a bovine heart that may have been treated with a crosslinking agent. The natural human heart valve, which is supposed to be fixed with the invention, is identified as the mitral valve. Therefore, the pericardium is used to replace the damaged or diseased naturally occurring heart valve. Also, such a valve can allow the pre-loading of the stent within a delivery system.

The valves are made using bovine pericardium. The ECM (Extracellular Matrix) tissue is generally harvested from the pericardial sac of cows and is then used to manufacture the leaflets. The tissue from pericardial sac is particularly well suited for a valve leaflet due to its durable physical properties. The tissues are glutaraldehyde fixed, non-viable, chemically treated (decellularized) and sterilized so that the biological markers are removed making them more compatible with the patient's immune system.

The potential benefits of bovine pericardium are superior biocompatibility, demonstrates minimal suture line bleeding and patency can be immediately confirmed by ultrasound, such as TEE ultrasound. They also have benefits like lack of calcification, support of cellular ingrowth and reduced rates of restenosis and infection. The pericardium is durable, strong and available in various sizes.

In order to seal the stent once put in place, the stent further comprises a skirt, which surrounds at least the dry valve. The skirt therefore provides sealing between the stent and the left ventricle of the heart. Said skirt comprises at least one of bovine pericardium and polyester, preferably of both of said materials.

To assist the fixation of the valve to the heart, the valve may further have a PET fabric skirt that attaches the tissue to the stent frame. PET material is highly inert and does not create any adverse reaction in human body. The PET material also permits ingrowth of cells into the cloth which helps hold the valve in place minimizing thrombosis at the same time.

Generally speaking PTFE suture lines may be used for fixation on fixing the stent to the heart.

The stent frame can further be made out of Nitinol. Nitinol is a collapsible and flexible metal, which is furthermore self-expandable and comprises a shape-memory.

Also, as already mentioned above, the stent can be divided into at least two sections, i. e. the first section and the second section, which are arranged adjacent to each other at a longitudinal axis. The lengths, sizes and dimensions of the respective sections are believed to be particularly suitable for a minimally invasive treatment of mitral valve diseases. Selecting the length appropriately may enable an interference fit between the stent and the mitral valve to be sufficient to prevent the stent from becoming dislodged in time.

According to an embodiment of the invention the hooks are formed by two adjacent arms, which are interconnected, in particular wherein a tip of the hook is formed by a vertex of the respective diamond shaped cell. In this connection it should be noted that the term vertex refers to a corner region of each cell, i.e. the region of the cell forming a corner where two respective sections of the arms meet. Preferably, the vertex at least substantially forms an origin of the corner where two respective sections of the arms meet. Also, a shape of said hooks can follow an outer shape of the first section of the stent, albeit lying radially further outwards than the outer shape of the stent. One could therefore claim that the hooks are arranged parallel to the outer shape of the first section.

The stent frame may further comprise additional struts arranged respectively formed at least at the second section and/or at a transition between the first and the second section, which extend outwardly beyond the web-like structure and face the first section to form additional anchors. Said additional struts can function like barbs which help fixing the stent at the position of the native mitral valve. Such barbs may help to fix the stent properly even under difficult conditions, i. e. for example, when a person is exposed to some kind of impact such as an accident or the like.

The amount of additional struts placed at the second section and/or at the transition between the first section and the second section may vary, i. e. may be chosen freely.

In some embodiments said additional struts may be chosen to be linear while in other embodiments the additional struts may follow an outer shape of the second section and/or an outer shape of the transition between the first and the second section.

A length of the struts may also be chosen freely. In this connection it is noted that the exact shape of the struts may be chosen depending on the length of the struts, i. e. longer struts may follow the outer shape of the second section and/or the transition while shorter struts may be linear.

Said additional struts may further be fixed at the connection points of the arms. That is, the struts may be fixed at the vertices which may comprise eyelets for that purpose. The fixation of the struts at such eyelets at at least some of the vertices between the individual arms renders the stent more flexible. This is because the eyelets are generally less rigid than points of connection of prior art design.

According to another embodiment of the invention, at the transition between the first and second sections, all of the arms of the first section extend outwardly with respect to the second section since the maximum outer diameter of the first section is larger than the maximum outer diameter of the second section.

The first section may further comprise part of a generally balloon like outer shape, and the second section may comprise a generally cylindrical shape. It could be shown that such shapes can help to improve the interference fit of the stent with the native mitral valve such that the stent can be held in place properly once it is deployed.

According to another embodiment ends of the arms of the first section may face radially inwards, and/or ends of the arms of the second section may be arranged coaxially with the longitudinal axis, i.e. parallel to the longitudinal axis. Such an arrangement prevents the ends of the arms to poke the heart walls during deployment and/or after the stent is being expanded.

According to still another embodiment at least some of the cells of the first section are larger than the cells of the second section. This may be caused by the fact that the maximum outer diameter of the first section is larger than the maximum outer diameter of the second section. Hence, the cells may simply be larger because of the web-like structure being stretched out more at the first section than at the second section.

The dry valve may further comprise between two and six leaflets, preferably three or four leaflets, with the leaflets being fixed to the stent frame at fixation points at the second section. It has shown that for stents shaped circularly in the region of attachment of the valve, a valve comprising three leaflets is the best option in order to distribute the forces of the blood flow present in the heart evenly during the opening and closing process of the valve. Nevertheless, the exact number of leaflets may be chosen according to the application, the medical condition, the anatomical properties of the patient and so on. The fixation points of the second section may be eyelets to which the leaflets can be sutured.

The dry bovine pericardium may have a maximum tensile stress selected in the range of 20 to 25 MPa, and/or wherein the rehydrated bovine pericardium has a tensile stress selected in the range of 12 to 15 MPa. Thus, the dry bovine pericardium can comprise a tensile resistance which can be up to 15 times higher than the tensile resistance of the leaflets of a human heart. This is mainly done for safety reasons in order to minimize tearing or fracture of the pericardium.

The mechanical properties of a material, in particular tensile strength, can be tested under strain-stress evaluation using Universal Testing Machine (Oswaldo Filizzola, model AME-2kN).

Also, the dry bovine pericardium may have a calcium content selected in the range of 0.01 to 0.1 g/Kg. The bovine leaflets may generally be as flexible and durable similar to the patient's natural tissue and therefor individual with such replacement valve may not require blood thinner medication on a continuous basis. Bovine pericardium tissue provides better hemodynamics in view of their similarity to natural flexible leaflet valves, some bovine pericardium valves may have some limitation on durability due to calcification and degeneration process. Treating the valves with a specialized anticalcification treatment makes them more resistant to calcification. The valves having such a calcium content are hence more resistant to calcification and are more durable.

According to another embodiment of the invention the dry bovine pericardium is formed using a method of treatment comprising the following steps:

(1) soaking of the bovine pericardium treated with a crosslinking agent with a saline solution;
(2) contacting the soaked bovine pericardium with an aqueous solution comprising Hydrogen Peroxide;
(3) contacting the bovine pericardium with an aqueous solution comprising PBS and EDTA;
(4) contacting the bovine pericardium with a solution comprising glycerol, ethanol and EDTA; and
(5) contacting the bovine pericardium with a glycerol solution.

One embodiment of the present invention utilizes soaking of the bovine pericardium treated with a crosslinking agent with a saline solution.

As used herein, a crosslinking agent is glutaraldehyde which is preferably used in biochemical and medicine applications as an amine-reactive homobifunctional crosslinker. Glutaraldehyde treatment produces stable cross-links in cellular and extra-cellular matrix proteins which substantially reduced graft immunogenicity. However, such tissue has altered mechanical properties, early mechanical failure, cytotoxicity, and incomplete suppression of immunological recognition. Besides this severe calcification was noticed in glutaraldehyde-treated bovine pericardium. An emerging alternative to glutaraldehyde treatment is further treatment according to the method steps, i.e. a method allowing to reduce calcification of the bovine pericardium.

It is preferably to use the crosslinking agent in an amount of from 0.1% to 5.0% by volume, more preferably from 0.2% to 3.0% by volume, further preferably from 0.3% to 2.0% by volume and especially preferably from 0.5% to 1.0% by volume.

In this respect, as a first step a soaking of the bovine pericardium with an aqueous saline solution comprising 0.9% of sodium chloride (9.0 g per litre) is carried out. Such a solution is also commonly named as normal saline, physiological saline or isotonic saline solution.

In a second step, the soaked bovine pericardium is contacted with an aqueous solution comprising Hydrogen Peroxide. It is preferred that the concentration of hydrogen peroxide is from 0.05% by volume to 5.0% by volume, preferably from 0.1% by volume to 3.0% by volume, more preferably from 0.2% by volume to 2.0% by volume.

In a third step of the present invention, the bovine pericardium is contacted with an aqueous solution comprising PBS and EDTA.

As used herein, the term "contacting" means treating, immersion, exposing to, rinsing of the biological tissue used in the inventive method.

As used herein, the term "PBS" is directed to a phosphate buffered saline having a pH of 7.4 and containing a water based salt solution of disodium hydrogen phosphate, sodium chloride and, in some formulations, potassium chloride and potassium dihydrogen phosphate. PBS is used in biological and medical applications, such as washing cells, transportation of tissues and dilutions, because PBS closely mimics the pH, osmolarity, and ion concentrations of the human body.

The term "aqueous solution" refers to a solution comprising a substance or a compound and water that has been purified to remove contaminants which are able to influence the end product. Preferably, distilled water, double distilled water or deionized water is used in a method of the present invention.

The term "EDTA" is used herein to refer to ethylenediaminetetraacetic acid which is a complexing chelating agent being able to sequester metal ions especially like $Fe^{2+}/Fe^{3+}$, $Al^{3+}$, $Mg^{2+}$, $Ca^{2+}$, $Mn^{2+}$, $Zn^{2+}$ and others and to remove them from the solution forming so called EDTA-complexes.

According to embodiment, it is especially important to remove calcium ions from the solution by forming calcium chelator that has been shown to inhibit mineralization of biological tissues, in particular bovine pericardium tissue. It is suggested that EDTA binds to calcium ions on the outer shell of hydroxyapatite crystals which are formed from calcium phosphate crystals thereby chelating and removing calcium ions from the crystals, causing the tissue material to shrink thus demineralizing the material.

Treatment of biological tissues with EDTA hence slows down the progression of calcification by binding calcium before it can react to form hydroxyapatite. Since the calcification of biological tissues used e.g. as bioprosthetic heart valves is a clinically significant problem that contributes to implant failure, it is of significant importance to reduce calcium level in biological tissues used as an implant. Therefore, in the present invention, the EDTA treatment can reduce calcium level in biological tissues, especially in bovine or porcine pericardium or a heart valve preferably by 20%, more preferably by 30%, further preferably by 40% and especially preferably by 50%. Further, it is preferable to use EDTA in combination with PBS in order to increase demineralization and compatibility with a human body.

Furthermore, it is preferable to use EDTA, in particular in steps (3) and (4), having a concentration of more than 0.01% by weight, preferably of more than 0.05% by weight, more preferably of more than 0.10% by weight, still preferably of more than 0.15% by weight, and of less than 10.0% by weight, preferably of less than 8.0% by weight, more preferably of less than 6.0% by weight, still preferably of less than 5.0% by weight, further preferably of less than 3.0% by weight. Still further in the present invention, it is preferably to use disodium EDTA.

In a fourth step of the present invention, the bovine pericardium is contacted with a solution comprising glycerol, ethanol and EDTA, and in a fifth step the bovine pericardium is contacted with a glycerol solution in order to further reduce calcification of biological tissue and to dehydrate the bovine pericardium. The following steps describe an implementation of these processes in the method.

After the bovine pericardium has been processed through steps (1) to (3) of the method, they undergo the treatment in a solution comprising glycerol, ethanol and EDTA.

Phospholipids in and around biological tissue cells have been found the most prominent calcification nucleation sites. Therefore, the removal of these tissue components has been proposed to reduce mineralization, in particular calcification. Different studies have shown these to be effective calcification prevention strategies. The organic solvents like ethanol or glycerol or a mixture of ethanol and glycerol can be similarly used for this purpose. For example, the treatment with at least 70% ethanol, preferably with at least 80% ethanol, more preferably with at least 90% ethanol, extracts phospholipids from the tissue while also causing a change in collagen conformation that increases bioprosthesis resistance to collagenase. Thus, ethanol treatment allows extracting almost all phospholipids and cholesterols from the bioprosthesis, thus eliminating calcification of the biological tissue cells. Additionally, ethanol treatment also prevents adsorption of phospholipids and cholesterols from the solution. The method by which glycerol fixes biological tissue is not jet fully understood, but a 98% concentration, preferably 99% concentration, is sufficient to treat the biological tissue to make the tissue more biocompatible and resistant to calcification.

In this respect, it is preferably to treat biological tissue in a solution comprising glycerol, ethanol and EDTA for at least 60 minutes, preferably for at least 75 minutes, more preferably for at least 90 minutes, at room temperature, in particular at a temperature of 10° C. to 25° C., preferably at a temperature of 15° C. to 25° C., more preferably at a temperature of 18° C. to 22° C., under stirring of not more than 500 rpm, preferably of not more than 300 rpm, more preferably of not more than 50 rpm. During this time most of the water molecules presented in biological tissue, in particular pericardial tissue, are replaced with glycerol.

Furthermore, it is preferable to use a mixture of glycerol and ethanol, wherein a volume ratio of glycerol to ethanol is preferably from 1:5 to 5:1, more preferably from 1:4 to 4:1, still preferably from 1:3 to 3:1, further preferably from 1:2 to 2:1.

The bovine pericardium is then removed from the solution and placed in glycerol for further dehydration for at least 60 minutes, preferably for at least 75 minutes, more preferably for at least 90 minutes, at room temperature, in particular at a temperature of 10° C. to 25° C., preferably at a temperature of 15° C. to 25° C., more preferably at a temperature of 18° C. to 22° C., under stirring of not more than 500 rpm, preferably of not more than 300 rpm, more preferably of not more than 50 rpm.

It can further be preferable to use an additional step of contacting or rinsing the bovine pericardium with ethanol having a concentration of at least 70% by volume, preferably with at least 80% by volume, more preferably with at least 90% by volume. The additional step, in particular step (3a), is preferably carried out before contacting the biological tissue with a solution comprising glycerol, ethanol and EDTA. It can further be preferable to carry out another additional step (5a) of contacting the biological tissue with ethanol after the step of contacting the biological tissue with a glycerol and before the step of drying the biological tissue. It can still further be preferable to carry out an additional step (3a) and/or (5a) using a mixture of ethanol and EDTA having a concentration as in step (3) or (4).

The bovine pericardium is removed from the solution and exposed to ambient air or an inert environment, e.g. nitrogen, at room temperature and humidity so as not to adversely affect tissue properties. Preferably, the drying is performed in a clean room at ambient conditions for at least 12 hours, preferably for at least 16 hours, still preferably for at least 20 hours. Further preferably, the drying is performed under high efficiency particulate air (HEPA) filter, in particular under HEPA conditions in a clean room. As used herein, the term "ambient conditions" is directed to the ambient temperature of more than 10° C., preferably of more than 12° C., more preferably of more than 14° C., especially preferably of more than 18° C., and preferably of less than 25° C., more preferably of less than 23° C., further preferably of less than 22° C. Further in the present invention it is preferably to carry out each of steps (1) to (7) at the ambient conditions as described above.

The treated and dried bovine pericardium is then packaged in a container or package essentially free of liquid for subsequent surgical implantation. As used herein, the term "essentially free of liquid" means a non-fluid environment in which the presence of water or other substances is limited to approximately the content of such substances in ambient air.

According to a further embodiment the skirt is arranged to cover at least the second section, preferably also the first section, in particular the whole stent, from within. The skirt may cover at least the region, which is occupied by the valve. Usually, in order to provide a better sealing, a length of the skirt is longer than a length of the valve. In some embodiments the skirt may even cover the whole stent from within.

Once in place, the skirt will be pressed against the stent frame due to blood flow through the valve from the first section to the second section. Depending on the precise anatomy of the patient, the stents may comprise different sizes and thus also different skirt sizes. For some cases it may be better to have a longer skirt, which covers most parts of the stent while in other cases a short skirt, which covers only the second section and small parts of the first section, may be sufficient.

All ends of the arms at a first end and a second end may lie in a common plane to avoid having single arms that may poke the ventricle and/or the atrium.

According to a further embodiment the stent further comprises eyelets arranged at a first end of the first section for attaching the stent to a delivery device, which preferably project beyond said common plane of the ends of the arms, wherein the eyelets lie in a further common plane. The common plane is again provided for safety reasons. The eyelets for attaching the stent to a delivery device are provided to be able to deploy the stent at the mitral valve without having to perform an open-heart surgery.

The eyelets of the first section project inwardly with respect to the longitudinal axis with the eyelets in particular following the same contour as the ends of the stent of the first section remote from the transition. Since the mentioned eyelets are used to attach the stent to a delivery device during deployment, it may be advantageous to have the eyelets following the same contour as the ends of the stent such that they project inwardly in order to prevent the attachments to poke the arteries and/or veins while the stent is moved through the body to the heart.

The stent may also comprise additional means for attaching the stent frame to a point of interest, in particular the mitral valve, at the first section and/or the second section of the stent frame such that it can be ensured that the stent remains at its intended place. Such means can, for example, be further eyelets arranged at the ends of the arms. Said eyelets can either lie in the common plane spanned by the ends of the arms or can project beyond said plane. In the second case, the eyelets can lie in a common plane as well which may overlap with the common plane of the eyelets used for fixing the stent frame to the delivery device.

The stent may further comprise further eyelets at the second section, in particular at the ends of the arms at the second section, to attach the dry valve to the stent frame.

According to a second aspect of the invention a delivery device for delivering a self-expandable stent according to the invention is provided. The delivery device comprises a flush port, a main body part for holding, inflating and/or releasing the stent, and an actuation mechanism for moving the stent to a delivery site.

The device may be preloaded with a stent so that this can be stored ready to use on a shelf in a medical facility to significantly reduce the treatment time of acute aortic syndromes leading to reduced mortality rates of acute aortic syndromes.

The actuation mechanism may have a torque control and may be able to rotate the stent about an axis of the main body. In this way the stent can be positioned in relation to the extremities in an as good as possible manner at the mitral valve, to deploy the valve and stent at the desired delivery site. The device may further be improved with steerable control, to increase precision and accuracy at deployment.

Also, the device may have a knob or the like at the actuation mechanism, with the knob in particular being able to be rotated about an axis of rotation of the actuation mechanism. By turning the knob, the lumen is able to deflect and allows a better positioning of the tip and the main body of the delivery device and less stress over the system during deployment. This leads to an improved accuracy of deployment of the delivery device and hence of a stent that is delivered to a delivery site using the delivery device.

BRIEF DESCRIPTION OF THE DRAWINGS

The invention will be described in detail by means of embodiments and with reference to the drawings. These show preferred embodiments. The features described may be configured in various combinations, which are encompassed in this document. The drawings show.

DETAILED DESCRIPTION

Figure 1:
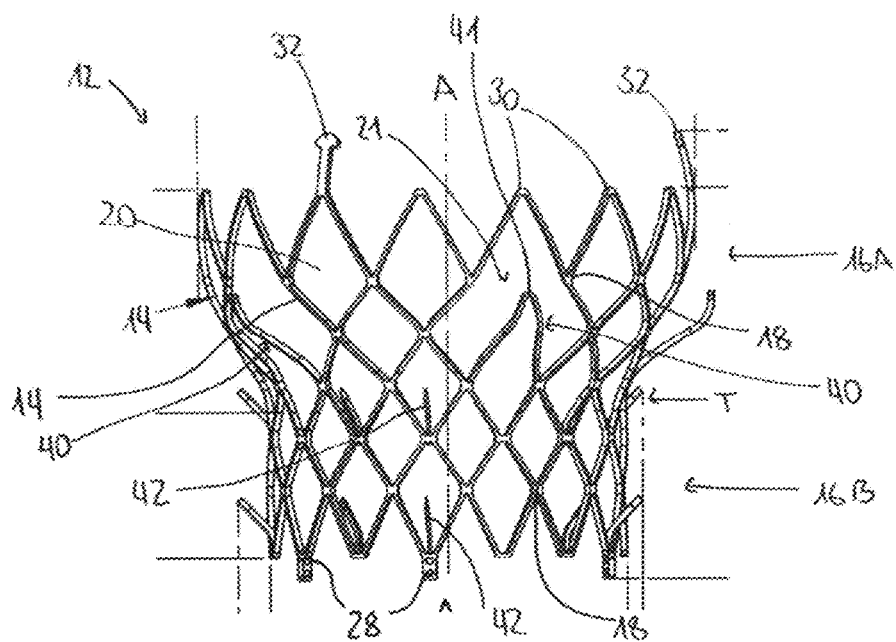
FIG. 1: a stent frame according to a first embodiment.
Figure 2:
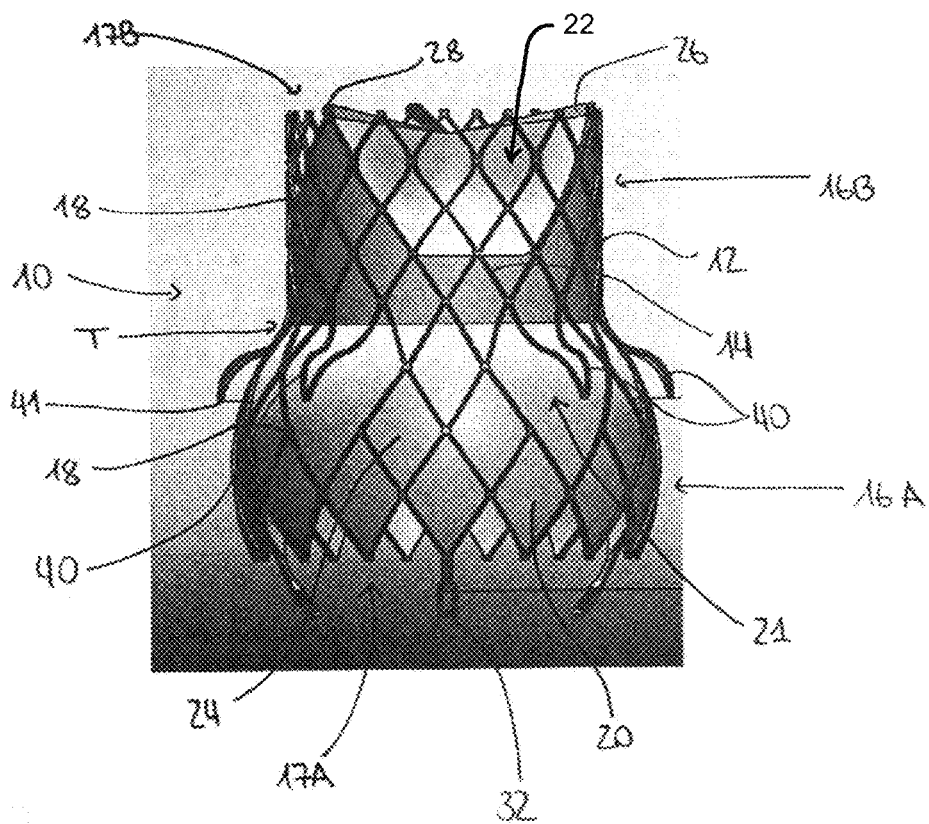
FIG. 2: the stent frame according to a second embodiment and further including a dry valve and a skirt.
Figure 3:
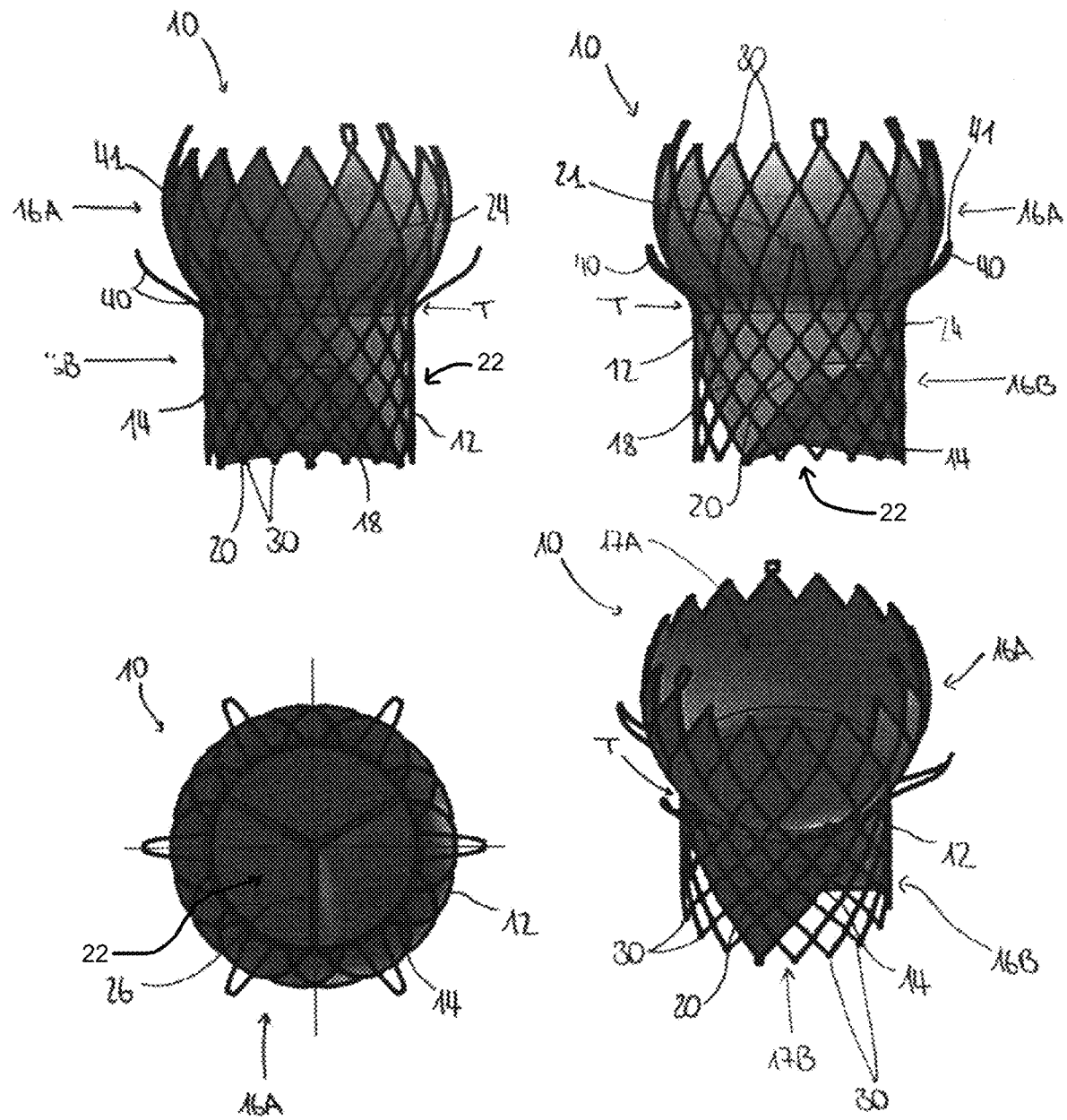
FIG. 3: different views of the stent of FIG. 2.

FIGS. 1 to 3 show different views of a self-expandable stent 10 configured to be placed at the mitral valve of a patient, with the stent 10 having a stent frame 12 composed of a plurality of different arms 14. The stent frame 12 is composed of Nitinol, which is a flexible material comprising shape-memory such that the stent 10 is able to self-expand once it is deployed. Hence, the stent 10 can be delivered in a compressed state to the mitral valve before it self-expands at a delivery site.

The frame 12 further comprises at least two sections, i. e. a first section 16A and second section 16B, arranged at a longitudinal axis A. The terms "first" and "second" refer to the direction of the blood flow through the stent once it is deployed at its intended place. Hence, once put in place, blood flows first through the first section 16A and then through the second section 16B of the stent 10. Additionally, the stent 10 comprises a transition T between the first section 16A and the second section 16B. All sections 16A, 16B and T are interconnected with each other.

The frame 12 is further characterized in that the arms 14 are connected to one another at a plurality of connection points 18 such that they form a web-like structure of diamond-shaped cells 20. As one can see in FIGS. 1 to 3 the stent 10 can be composed of rows of cells 20 arranged at the longitudinal axis A. The amount of rows of cells 20 can be chosen according to the anatomical conditions of the patient etc.

Each stent cell 20 in the present embodiments is formed of four sides and four vertices. The four sides of stent cells 20 are respectively formed by sections of the arms 14 and the vertices are either formed by an end of an arm 14 or a connection point 18.

As can be seen in FIGS. 1 to 3 some of the arms 14 of the stent 10 extend outwardly beyond the web-like structure of a main body of the stent frame 12 to form a hook 40 which faces the first section 16A. The cells 21, which are arranged underneath said hooks 40, comprise an, in particular significantly, larger area than the rest of the cells 20 of the stent frame. Said hooks 40 can act as anchors in order to attach the stent more tightly at the position of a native mitral valve which is supposed to be treated and/or replaced.

It can further be seen that the hooks 40 originate at the transition T between the first section 16A and the second section 16B. They are built by two adjacent arms 14, which are interconnected. In particular, a tip 41 of the hook 40 is formed by a vertex of the respective diamond-shaped cell 20. Furthermore, the shape of the hooks 40 generally follows the balloon-like shape of the first section 16A albeit comprising a larger diameter than the first section 16A.

In the embodiment of FIG. 1 the stent 10 further comprises additional struts 42 which are formed at the second section 16B and at the transition T. Said struts 42 also extend outwardly such that they function like barbs in order to fix the stent more accurately and securely to the heart. The struts 42 of the shown embodiment comprise a linear shape and a comparatively short length.

The length of the struts can be selected from the range of lengths comprising 25 to 75%, in particular 40 to 60% of a length of the respective cell 20 between two apexes of the cell 20 in parallel to the longitudinal axis A.

It can further be seen in FIG. 1 that the struts 42 are fixed at the connection points 18 of the arms 14. For this reason, said connection points may comprise eyelets (not shown) to which the struts 42 can be fixed to.

The second section 16B further comprises a valve 22 made out of dry bovine pericardium as well as a skirt 24 made out of dry bovine pericardium and polyester. The valve 22 usually comprises between two and six leaflets 26 which can be attached to the stent frame 12, for example, at eyelets 28 (see FIGS. 1 and 2) arranged at some 14 at a second end 17B of the stent frame 12. Consequently, the stent 10 further comprises a first end 17A at the first section 16A. In the depicted embodiment the valve 22 comprises three leaflets 26 which are attached to three arms 14 at the second end 17B of the stent 10. As one can see in FIG. 1 it can be possible to provide two eyelets 28 at each arm 14. As one can also see, said eyelets 28 are provided at the position where two adjacent leaflets 26 meet such that both of said leaflets 26 can be sutured to one arm 14. Hence, with the two eyelets being provided at said one arm 14, the stent 10 comprises one eyelet 28 per leaflet 26 at each one of said arms 14.

The eyelets 28 are arranged such that they are positioned at apexes between two directly adjacent leaflets 26, with the region of the respective leaflets 26 at the apexes being fixed to the eyelets 28 in order to stabilize the dry valve 22 in this region to ensure a correct functioning, i. e. opening and closing, of the leaflets 26 even in the region of the apexes.

Generally speaking, also every arm 14 could be provided with eyelets 28. The exact number of arms 14 which will be provided with eyelets 28 may be chosen according to the application. For example, if a valve 22 with only two leaflets 26 is chosen to be placed inside the stent 10, only two arms 14 may be provided with eyelets 28. In some embodiments, on the other hand, the eyelets 28 can always be provided at two adjacent arms 14 in order to fix two adjacent leaflets 26 to the stent frame 12 (see FIG. 2).

Due to anatomical reasons of the left ventricle and left atrium of the heart, the skirt 24 does not only surround the valve 22 at the second section 16B but may cover up to 100% of the stent 10 to prevent leakage between the stent 10 and the heart of the patient. In the embodiments of FIGS. 2 and 3, for example, most of the cells 20 are covered by the skirt 24. Only some of the cells 20 of the second section 16B are covered by the skirt 24 while others are being left out, namely the ones between the leaflets 26.

An outer contour of the stent 10 according to the invention can be described as being balloon shaped at the first section 16A and cylindrical at the second section 16B. Starting from the first end 17A the first section 16A then transitions into the transition T into the second section 16B. It can be seen that the maximum outer diameter of the first section 16A is significantly larger than the maximum outer diameter of the second section 16B.

Generally speaking the outer contour is selected to adapt to the shape of the valve into which it is fitted in order to be adapted to create a tight interference fit with the mitral valve 22 to ensure that the positioning of the stent 10 does not vary in time. This interference fit may add minor, but additional, stability to the valve 22 once positioned.

In order to attach the stent 10 at its respective point of interest, i. e. the mitral valve, the stent 10 can comprise further eyelets (not shown) at its respective first and second ends 17A, 17B. That is, after being expanded, the stent 10 does not only hold itself in place by fitting into the mitral valve but also by being sutured to the walls of the heart. The exact attachment point and technique can be chosen according to the different conditions inside the different hearts which are being treated with the invention.

The ends 30 of the arms 14 at both ends of the stent 10 can lie in a common plane. The eyelets, which are used to attach the stent to the mitral valve (not shown) can comprise a rectangular outer shape with a rectangular opening for suturing the stent 10 to the aortic artery. Generally, said eyelets can also comprise a different shape, e. g. a circular shape, for both their outer and inner shape. The eyelets 28 as well as the eyelets for suturing the stent 10 to the artery can project beyond sad common plane of the ends 30 of the arms 14 and span another common plane.

Additionally, the stent 10 comprises eyelets 32 for attaching the stent 10 to a delivery device (see FIG. 1) which also project beyond the common plane of the ends 30 of the arms 14.

Figure 4:
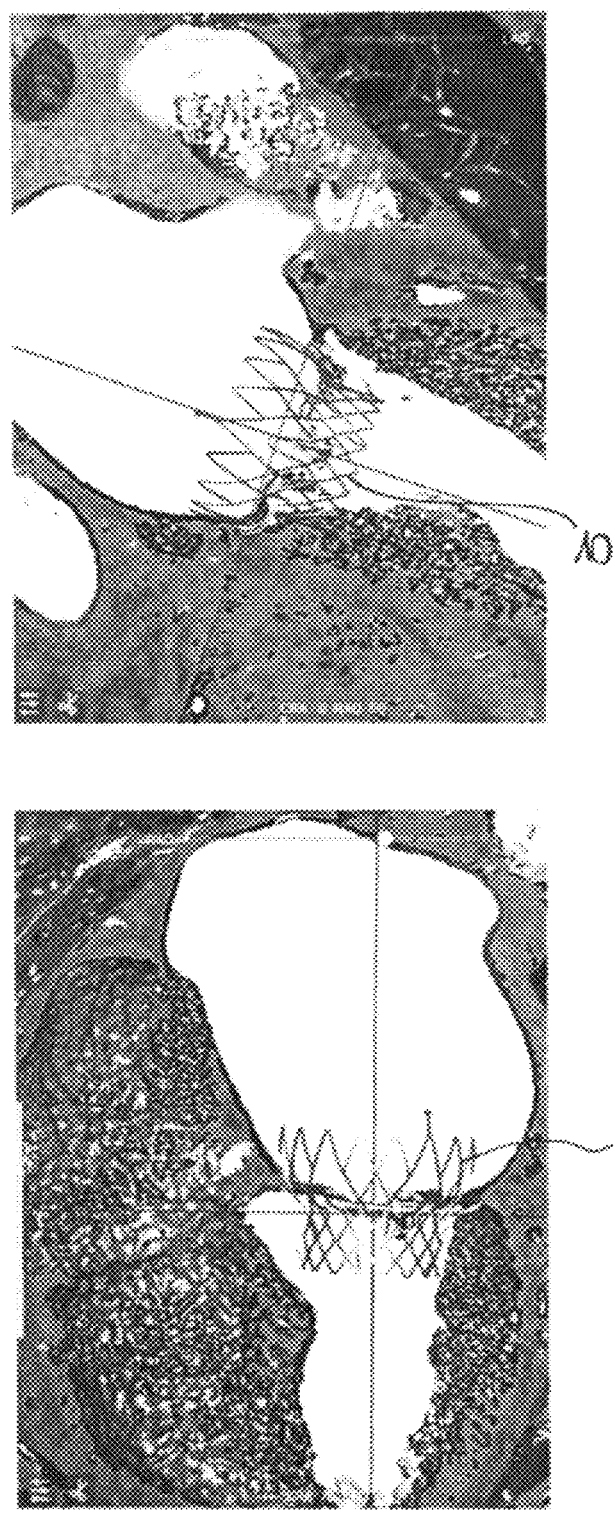
FIG. 4: CT reconstruction pictures of a deployed stent.
Figure 5:
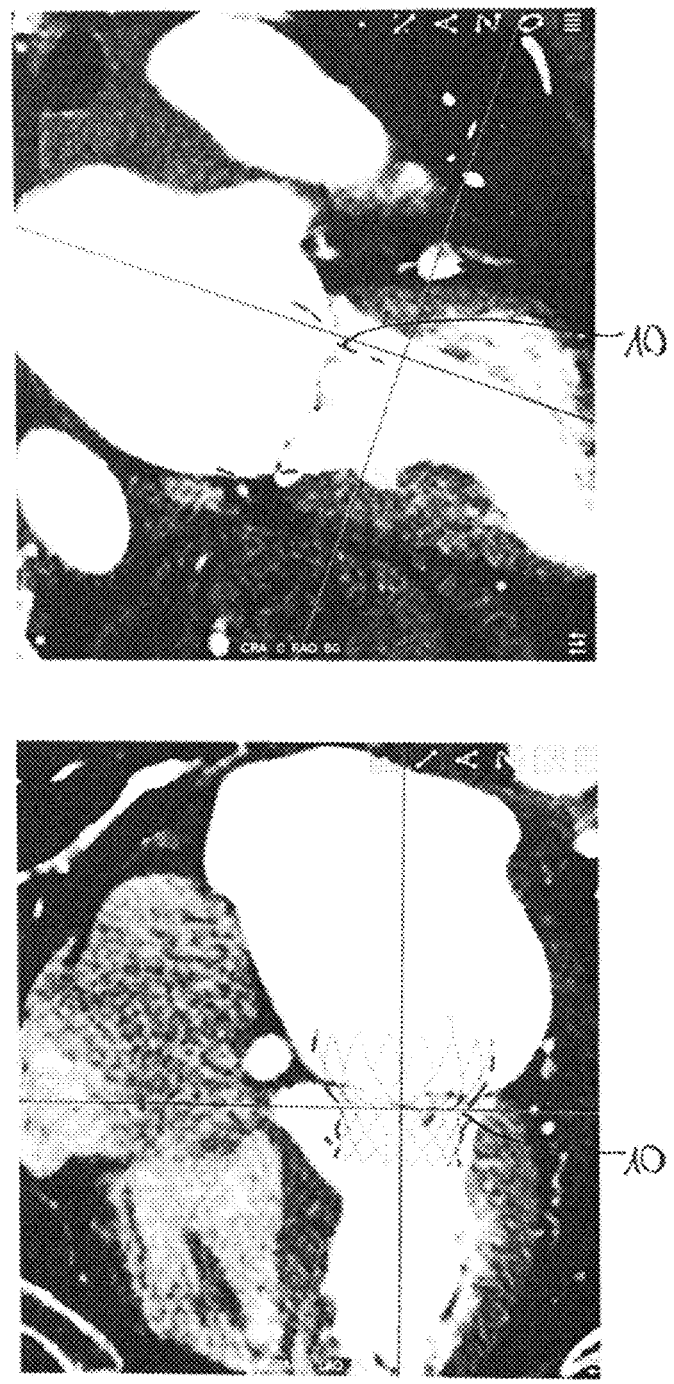
FIG. 5: CT reconstruction pictures of the deployed stent of FIG. 4 from different angles.

Finally, in FIGS. 4 and 5 one can see different CT pictures of a stent 10, which has been deployed at the mitral valve of a patient, preferably using a delivery device as described in the foregoing. Such delivery devices are common state of the art and are therefore not described in detail. The different pictures in FIGS. 4 and 5 show the same stent 10 from different angles. As one can see in those CT pictures, the stent 10 is in the expanded state and has been deployed at the native mitral valve of the patient in order to replace it.

REFERENCE LISTING 10 stent
12 frame
14 arms
16A first section
16B second section
17A first end
17B second end
18 connection point
20 cell
21 bigger cell
22 valve
24 skirt
26 leaflet
28 eyelet
30 end of arms
32 eyelets
40 hooks
41 tip
42 struts
A longitudinal axis
T transition

What is claimed is:

1. A self-expendable stent for placement at a mitral annulus that is self-expandable from an undeployed state to a deployed state comprising a stent frame having at least a first section and a second section arranged at a longitudinal axis of the stent, wherein the stent frame is formed by a plurality of endless arms, said endless arms being connected to one another at connection points forming a web-like structure with diamond-shaped cells;
   a dry valve made out of bovine pericardium arranged at least at the second section of the stent with the dry bovine pericardium being configured to be rehydrated with a solution,
   a skirt surrounding the dry valve and comprising at least one of bovine pericardium and polyester, and
   wherein, in the deployed state, a maximum outer diameter of the first section is larger than a maximum outer diameter of the second section, and
   wherein at least at a transition between the first section and the second section some of the endless arms extend outwardly beyond the web-like structure to form at least one hook, which faces the first section, wherein a tip of the at least one hook is an interconnection point of two adjacent endless arms,
   wherein the stent frame further comprises additional struts arranged at the second section, which extend outwardly beyond the web-like structure and face the first section to form additional anchors.

2. The self-expendable stent according to claim 1, wherein the tip of each of the at least one hooks is formed by a vertex of the respective diamond shaped cell.

3. The self-expendable stent according to claim 1, wherein the stent frame further comprises additional struts arranged at the transition between the first and the second section, which extend outwardly beyond the web-like structure and face the first section to form additional anchors.

4. The self-expendable stent according to claim 3, wherein said additional struts are fixed at the connection points of the endless arms.

5. The self-expendable stent according to claim 1, wherein, at the transition between the first and second sections, all of the endless arms extend outwardly with respect to the second section.

6. The self-expendable stent according to claim 1, wherein the first section comprises a balloon like outer shape.

7. The self-expendable stent according to claim 1, wherein the second section comprises a cylindrical shape.

8. The self-expendable stent according to claim 1, wherein the endless arms face radially inwards at a first end of the first section.

9. The self-expendable stent according to claim 1, wherein the endless arms are arranged coaxially with the longitudinal axis, i.e. parallel to the longitudinal axis, at a second end of the second section.

10. The self-expendable stent according to claim 1, wherein at least some of the diamond-shaped cells of the first section are larger than the diamond-shaped cells of the second section.

11. The self-expendable stent according to claim 1, wherein the dry valve comprises between two and six leaflets, with the leaflets being fixed to the stent frame at fixation points at the second section.

12. The self-expendable stent according to claim 11, wherein the dry valve comprises three or four leaflets.

13. The self-expendable stent according to claim 1, wherein the dry bovine pericardium has a maximum tensile stress selected in the range of 20 to 25 MPa.

14. The self-expendable stent according to claim 1, wherein the rehydrated bovine pericardium has a tensile stress selected in the range of 12 to 15 MPa.

15. The self-expendable stent according to claim 1, wherein the skirt is arranged to cover at least the second section from within.

16. The self-expendable stent according to claim 14, wherein the skirt is arranged to cover also the first section from within.

17. The self-expendable stent according to claim 14, wherein the skirt is arranged to cover the whole stent frame from within.

18. The self-expendable stent according to claim 1, wherein all of the endless arms at a first end and a second end of the stent lie in a first common plane.

19. The self-expendable stent according to claim 18, wherein the stent further comprises eyelets arranged at a first end of the first section for attaching the stent to a delivery device, wherein the eyelets lie in a second common plane.

20. The self-expendable stent according to claim 19, wherein the eyelets are arranged to project beyond the first common plane of the endless arms of the stent.

21. The self-expendable stent according to claim 19, wherein the eyelets of the first section project inwardly with respect to the longitudinal axis.

22. The self-expendable stent according to claim 19, wherein the eyelets follow the same contour as the endless arms of the first section remote from the transition.

* * * * *